United States Patent
Brenner et al.

(10) Patent No.: US 6,509,406 B1
(45) Date of Patent: Jan. 21, 2003

(54) PLASTIC MOLDING MATERIALS WHICH CAN BE DETECTED BY X-RAY CONTRAST

(75) Inventors: Axel Brenner, Düsseldorf (DE); Martin Döbler, Düsseldorf (DE); Michael Prein, Brasschaat (BE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/857,389

(22) PCT Filed: Dec. 1, 1999

(86) PCT No.: PCT/EP99/09336
§ 371 (c)(1), (2), (4) Date: Jun. 1, 2001

(87) PCT Pub. No.: WO00/36002
PCT Pub. Date: Jun. 22, 2000

(30) Foreign Application Priority Data

Dec. 11, 1998 (DE) .......................................... 198 57 149

(51) Int. Cl.⁷ .............................. C08J 3/00; C08K 5/13; C08K 5/02; C08L 69/00; A61K 6/08
(52) U.S. Cl. ........................ 524/462; 524/165; 524/341; 524/463; 523/117; 424/9.411; 424/9.45; 424/9.451
(58) Field of Search ................................ 524/462, 165, 524/341, 463; 523/117; 424/9.411, 9.451, 9.45

(56) References Cited

U.S. PATENT DOCUMENTS

| | | | |
|---|---|---|---|
| 3,361,700 A | 1/1968 | Archer et al. | 260/31.4 |
| 3,382,207 A | 5/1968 | Jaquiss | 260/45.7 |
| 3,645,955 A | 2/1972 | Flynn | 260/31.4 |
| 3,715,331 A * | 2/1973 | Molnar | |
| 4,283,447 A | 8/1981 | Flynn | 428/36 |
| 6,057,394 A | 5/2000 | Bödiger et al. | 524/423 |

FOREIGN PATENT DOCUMENTS

| | | |
|---|---|---|
| DE | 21 21 480 | 12/1971 |
| DE | 27 46 906 | 8/1978 |
| DE | 197 26 191 | 12/1998 |
| EP | 0 684 222 | 11/1995 |
| FR | 2223403 | 11/1974 |
| WO | 98/59005 | 12/1998 |

OTHER PUBLICATIONS

Eencyclopedia of Polymer Science & Engineering, vol. 14, (month unavailable), 1988, pp. 1–8, Ruth Silberman–Hazony Consultant, Radiopaque Polymers.

* cited by examiner

Primary Examiner—Patrick D. Niland
(74) Attorney, Agent, or Firm—Joseph C. Gil; Noland J. Cheung; Aron Preis

(57) ABSTRACT

The invention provides X-ray contrastable plastics materials with low-molecular weight iodine compounds, a process for preparing X-ray contrastable plastics materials with low molecular weight iodine compounds, the use of low molecular weight iodine compounds to improve the X-ray contrast in transparent plastics materials and toys with improved X-ray contrast containing low molecular weight iodine compounds.

2 Claims, No Drawings

PLASTIC MOLDING MATERIALS WHICH CAN BE DETECTED BY X-RAY CONTRAST

The invention provides X-ray contrastable plastics materials with low-molecular weight iodine compounds, a process for preparing X-ray contrastable moulding compositions with low molecular weight iodine compounds, the use of low molecular weight iodine compounds to improve the X-ray contrast in transparent plastics materials and toys with improved X-ray contrast containing low molecular weight iodine compounds.

Materials with the highest possible transparency and good mechanical characteristics which can be detected in the body by using X-rays are sought for the medical field and also for children's toys. In contrast to metallic items, toys made of plastics are generally not detectable on an X-ray image. These types of moulding compositions can be made X-ray contrastable by means of suitable additives.

These types of moulding compositions were described, for example, in DE-A 195 45 289. In that patent, X-ray contrastable thermoplastic moulding compositions made of ABS with a $BaSO_4$ additive were described.

X-ray detectable moulding compositions were also described in Silberman-Hazony, Encycl. Polym. Sci. Eng. (1988), 14, 1–8. Thermoplastic materials with various heavy metals as X-ray contrast agents were described. In addition, a halogen-containing terpolymer was mentioned.

Finally, FR 2223403 describes PVC and other vinyl polymers with iodine-containing salicylic acids, benzoic acids and their esters which resemble those in U.S. Pat. Nos. 3,361,700 and 3,645,955. However, PVC is not suitable for applications in which high transparency and good mechanical properties are required.

DE-A 197 26 191 and the patents U.S. Pat. No. 3,469,704 and DE-A 17 20 812 cited therein described transparent plastics moulding compositions made of polycarbonates with iodine-containing terminal groups. However, these can, under some circumstances, involve considerable additional synthesis costs because the polymer chains themselves have to be modified.

Finally, U.S. Pat. No. 3,382,207 discloses iodine-containing diphenyl carbonates as additives for polycarbonates.

Thus, the prior art does not currently provide any adequate X-ray contrastable plastics materials for use in transparent plastics parts. Due to its outstanding mechanical properties, polycarbonate has hitherto been used in particular for transparent toy parts which are subject to high mechanical stress. Now, it is intended to develop a type of plastics material that can be detected within the context of a conventional X-ray photograph while having unchanged high transparency and the smallest possible impairment to its mechanical properties. The thickness of layer in which the plastics material is still detectable should be as small as possible, but at most 1.2 mm.

The object was to develop moulding compositions using readily obtainable additives in standard thermoplastic materials which exhibit adequate contrast in X-ray images while also having good mechanical characteristics and transparency. The addition of heavy metals was to be avoided for toxicological reasons since materials for children's toys were being sought.

Accordingly, the present application provides X-ray contrastable plastics materials containing at least one low molecular weight iodine compound, characterised in that the iodine compound is present in amounts of 0.1 wt. % to 25 wt. % and is chosen from the lasses D-thyroxin, L-thyroxin, metrizamide, N,N'-bis-(2,3-dihydroxypropyl)-5-[N-(2,3-dihydroxypropyl)-acetamido]-3,4,6-triiodoisophthalamide, α-(2,4,6-triiodophenoxy)-butyric acid, beta-bromo-2,4,6-triiodophenetols, ethylene glycol-4-(iodophenyl)-methylether-methylether and aromatic compounds in accordance with the following general formulae (I), (II), (III)

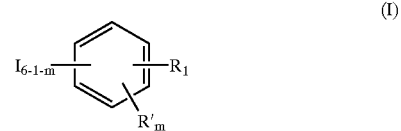

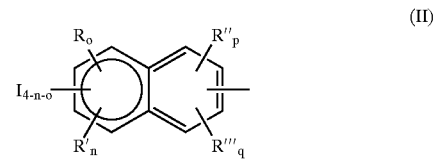

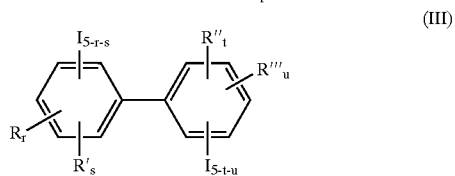

wherein R, R', R'', R'''=COOH, OH, NHCOR'''', CONHR'''', OR'''', Cl, Br, F, R'''', where R'''' may be H or a linear or branched alkyl group with 1–18 carbon atoms. Furthermore, l=0 to 5, m=0 to 5−l, n=0 to 3, o=0 to 3−n p=0 to 4, q=0 to 4−p, r=0 to 4, s=0 to 4−r, t=0 to 5, u=0 to 5−t.

To prepare metrizamide see J. Cell. Biol. 1991, 113, 45, to prepare Iohexol® (N,N'-bis-(2,3-dihydroxypropyl)-5-[N-(2,3-dihydroxypropyl)-acetamido]-3,4,6-triiodoisophthalamide) see Sigma-Aldrich Chemie GmbH, Steinheim, Germany, to prepare Baygnostil® (α-(2,4,6-triodophenoxy)butyric acid) see Bayer AG, Leverkusen, Germany.

Mixtures of all the iodine-containing compounds mentioned above are also suitable.

The following are particularly suitable: 4,4'-diiodobiphenyl, 2,3,5-triiodobenzoic acid, 2,4,6-triiodophenol, 4-iodophenol, 3-iodophenol, 2-iodophenol, 3,5-diiodosalicylic acid, 3,5-diiodo-2-hydroxybenzoic acid, 4-iodobenzoic acid, 3-iodobenzoic acid, 2-iodobenzoic acid, 2,6-dimethyl-4-iodophenol, 2-iodo-4-phenylphenol, 3,3'-diiodo-2,2',6,6'-tetramethyl-4,4'-biphenol, 2,6-diiodo-4-methylphenol, 3,5-diiodo-2-hydroxybenzoic acid, 2,4-dichloro-6-iodophenol, 1,4-dimethoxy-2,3-dimethyl-5-iodobenzene, 1,2-dimethoxy-4-iodobenzene, 2,2'-diiodo-4,4',5,5'-tetramethoxybiphenyl, 4-iodo-3-phenylanisol, 1,2-dimethoxy-3,4-dimethyl-5-iodobenzene, 2,2'-diodo-3,3'-dimethyl-4,4',5,5'-tetramethoxybiphenyl, 1,4-dimethoxy-2-iodo-5-methylbenzene, 1,2-dimethoxy-4-iodo-5-methylbenzene, 1,2-diiodo-4,5-dimethoxybenzene, 2,2'-diiodo-3,3',4,4',5,5'-hexamethoxybiphenyl, 2,2'-diiodo-4,4'-dimethoxy-3,3',5,5'-tetramethylbiphenyl, very particularly 4,4'-diiodobiphenyl.

The X-ray contrastable plastics materials contain the low molecular weight iodine compound in amounts between 0.5 and 20 wt. %, preferably between 0.8 and 10 wt. % and particularly preferably between 1 and 5 wt. %.

Transparent thermoplastic materials are preferably used as transparent plastics, particularly preferably the polymers of ethylenically unsaturated monomers and/or polycondensates of bifunctional reactive compounds.

Particularly suitable plastics are polycarbonates or copolycarbonates based on diphenols, polyacrylates or copolyacrylates and polymethacrylates or copolymethacrylates such as e.g. polymethylmethacrylate or copolymethylmethacrylate, or else copolymers with styrene such as e.g. transparent polystyrene/acrylonitrile (SAN), also transparent cycloolefins, polycondensates or copolycondensates of terephthalic acid, such as e.g. polyethylene terephthalate or copolyethylene terephthalate (PET or COPET) or glycol-modified PET.

A person skilled in the art produces exceptional results with polycarbonates or copolycarbonates.

Thermoplastic, aromatic polycarbonates in the context of the present invention are either homopolycarbonates or copolycarbonates; the polycarbonates may be linear or branched in a known manner.

These polycarbonates are prepared in a known manner from diphenols, carbonic acid derivatives, optional chain stoppers and optional branching agents.

Details of the preparation of polycarbonates have been presented in many patent documents over the last 40 years. By way of example, reference is made here only to Schnell, "Chemistry and Physics of Polycarbonates", Polymer Reviews, volume 9, Interscience Publishers, New York, London, Sydney, 1964, to D. Freitag, U. Grigo, P. R. Müller, H. Nouvertné, BAYER AG, "Polycarbonates" in Encyclopedia of Polymer Science and Engineering, volume 11, 2nd edition, 1988, pages 648–718 and finally to Drs. U. Grigo, K. Kirchner and P. R. Müller "Polycarbonate" in Becker/Braun, Kunststoff-Handbuch, vol. 3/1, Polycarbonate, Polyacetale, Polyester, Celluloseester, Carl Hanser Verlag, Munich, Vienna 1992, pages 117–299.

Suitable diphenols for preparing polycarbonates are, for example, hydroquinone, resorcinol, dihydroxydiphenyls, bis-(hydroxyphenyl)-alkanes, bis-(hydroxyphenyl)-cycloalkanes, bis-(hydroxyphenyl)-sulfides, bis-(hydroxyphenyl)-ethers, bis-(hydroxyphenyl)-ketones, bis-(hydroxyphenyl)-sulfones, bis-(hydroxyphenyl)-sulfoxides, $\alpha,\alpha'$-bis-(hydroxyphenyl)-diisopropylbenzenes, and their ring-alkylated and ring-halogenated compounds.

Preferred diphenols are 4,4'-dihydroxydiphenyl, 2,2-bis-(4-hydroxyphenyl)-propane, 2,4-bis-(4-hydroxyphenyl)-2-methylbutane, 1,1-bis-(4-hydroxyphenyl)-p-diisopropylbenzene, 2,2-bis-(3-methyl-4-hydroxyphenyl)-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, bis-(3,5-dimethyl-4-hydroxyphenyl)-sulfone, 2,4-bis-(3,5-dimethyl-4-hydroxyphenyl)-2-methylbutane, 1,1-bis-(3,5-dimethyl-4-hydroxyphenyl)-p-diisopropylbenzene, 2,2-bis-(3,5-dichloro-4-hydroxyphenyl)-propane, 2,2-bis-(3,5-dibromo-4-hydroxyphenyl)-propane and 1,1-bis-(4-hydroxyphenyl)-3,3,5-trimethylcyclohexane.

Particularly preferred diphenols are 2,2-bis-(4-hydroxyphenyl)-propane, 2,2-bis-(3,5-dimethyl-4-hydroxyphenyl)-propane, 2,2-bis-(3,5-dichloro-4-hydroxyphenyl)-propane, 2,2-bis-(3,5-dibromo-4-hydroxyphenyl)-propane, 1,1-bis-(4-hydroxyphenyl)-cyclohexane and 1,1-bis-(4-hydroxyphenyl)-3,3,5-trimethylcyclohexane.

These and other suitable diphenols are described, for example, in U.S. Pat. Nos. 3,028,635, 2,999,835, 3,148,172, 2,991,273, 3,271,367, 4,982,014 and 2,999,846, in German patent documents 1 570 703, 2 063 050, 2 036 052, 2 211 956 and 3 832 396, in French patent document 1 561 518, in the monograph "H. Schnell, Chemistry and Physics of Polycarbonates, Interscience Publishers, New York 1964" and in Japanese patent documents 62039/1986, 62040/1986 and 105550/1986.

In the case of homopolycarbonates, only one diphenol is used; in the case of copolycarbonates, several diphenols are used.

Suitable carbonic acid derivatives are, for example, phosgene or diphenyl carbonate.

Suitable chain stoppers are either monophenols or monocarboxylic acids. Suitable monophenols are phenol itself, alkylphenols such as cresols, p-tert.-butylphenol, p-n-octylphenol, p-iso-octylphenol, p-n-nonylphenol and p-iso-nonylphenol, halogenophenols such as p-chlorophenol, 2,4-dichlorophenol, p-bromophenol and 2,4,6-tribromophenol and mixtures of these.

The preferred chain stopper is p-tert.-butylphenol.

Suitable monocarboxylic acids are benzoic acid, alkylbenzoic acids and halogenobenzoic acids.

Preferred chain stoppers are phenols of the formula (I)

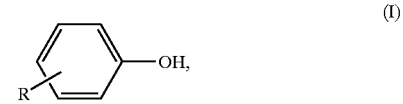

(I)

in which R is hydrogen, tert.-butyl or a branched or unbranched $C_8$ and/or $C_9$ alkyl group.

The amount of chain stopper to be used is 0.1 mol. % to 5 mol. %, with respect to the particular diphenols used. The addition of chain stoppers may take place before, during or after phosgenation.

Suitable branching agents are the trifunctional or more than trifunctional compounds known from polycarbonate chemistry, in particular those with three or more than three phenolic OH groups.

Suitable branching agents are, for example, phloroglucine, 4,6-dimethyl-2,4,6-tri-(4-hydroxyphenyl)-hept-2-ene, 4,6-dimethyl-2,4,6-tri-(4-hydroxyphenyl)-heptane, 1,3,5-tri-(4-hydroxyphenyl)-benzene, 1,1,1-tri-(4-hydroxyphenyl)-ethane, tri-(4-hydroxyphenyl)-phenylmethane, 2,2-bis-[4,4-bis-(4-hydroxyphenyl)-cyclohexyl]-propane, 2,4-bis-(4-hydroxyphenyl-isopropyl)-phenol, 2,6-bis-(2-hydroxy-5'-methylbenzyl)-4-methylphenol, 2-(4-hydroxyphenyl)-2-(2,4-dihydroxyphenyl)-propane, hexa-(4-(4-hydroxyphenyl-isopropyl)-phenyl orthoterephthalate, tetra-(4-hydroxyphenyl)-methane, tetra-(4-(4-hydroxyphenyl-isopropyl)-phenoxy)-methane and 1,4-bis-(4',4"-dihydroxytriphenyl)-methyl)-benzene and also 2,4-dihydroxybenzoic acid, trimesic acid, cyanuric chloride and 3,3-bis-(3-methyl-4-hydroxyphenyl)-2-oxo-2, 3-hydroindole.

The amount of optionally used branching agent is 0.05 mol. % to 2 mol. %, again with respect to the particular diphenols used.

The branching agent may either be initially introduced in the aqueous alkaline phase with the diphenols and the chain stoppers or may be added before phosgenation, dissolved in an organic solvent. In the case of a transesterification process, the branching agent is used together with the diphenols.

All these steps for preparing thermoplastic polycarbonates are familiar to a person skilled in the art.

Naturally, the plastics material makes up the major proportion of the compositions so that it is generally present in amounts between 75.0 and 99.9 wt. %, preferably 80 and 99.8 wt. %, particularly preferably between 90 and 99.2 wt. % and very particularly preferably between 95 and 99 wt. %, with respect to the entire mixture.

In order to achieve improved formulations, it is possible that in addition at least further additive which is conventionally present in thermoplastic plastics, preferably polycarbonates and copolycarbonates is also present, such as e.g. stabilisers (such as described e.g. in EP 0 839 623 A1 or EP 0 500 496 A1), especially heat stabilisers, in particular organic phosphites or phosphines, mould release agents, for example fatty acid esters of glycerine or tetramethanolmethane, wherein unsaturated fatty acid may also be fully or partly epoxidised, in particular glycerine monostearate or pentaerythrityl tetrastearate (PETS), flame retardants, antistatic agents, UV absorbers, for example triazoles, fillers, foaming agents, colorants, pigments, optical brighteners, transesterification catalysts and nucleating agents etc., preferably in amounts of up to 5 wt. % each, preferably 0.01 to 5 wt. %, with respect to the entire mixture, particularly preferably 0.01 to 1 wt. % with respect to the amount of plastics material as described, for example, in EP 0 839 623 A1 or EP 0 500 496 A1.

Mixtures of these additives are also possible.

The X-ray opaque polymer compositions obtained in this way may be converted into shaped items such as, for example, toy parts, but also fibres, films, strips, sheets, multi-wall sheets, vessels, pipes and other sections, using conventional methods such as, for example, hot compression, spinning, extrusion or injection moulding. The polymer compositions may also be processed to give cast films. The invention therefore also provides use of the polymer compositions according to the invention to produce a shaped item. The use of multi-layered systems is also of interest. In this case, a polymer composition according to the invention with a relatively high concentration of bromine or iodine-containing additives is applied in a thin layer to a shaped item made from a polymer which is X-ray transparent. Application may take place at the same time as or immediately after shaping the underlying item, e.g. by coextrusion or multi-component injection moulding. Application may also take place, however, to the final shaped underlying item, e.g. by lamination with a film or by coating with a solution. The moulding compositions are especially suitable for transparent children's toy parts or for medical applications. Such moulded parts are especially suitable for small parts of children's toys.

EXAMPLES

Example 1

94.7 parts of Makrolon 2808® are compounded together with 0.3 parts of PETS and 5 parts of 4,4'-diiodobiphenyl at 280° C. using a twin-screw extruder and then extruded to give test rods of various thicknesses. The properties of these moulded items are summarised in table 1:

TABLE 1

E-modulus: 2840 MPa
Elongation at break: 100%
Notched impact capacity according to Izod 180-1a: 8
Iodine content of moulded item: 2.9%
Test rod 1.2 mm thick: X-ray detectable with a dose of 0.1 rad
Test rod 1.6 mm thick: X-ray detectable with a dose of 0.1 rad
Test rod 2.4 mm thick: X-ray detectable with a dose of 0.1 rad
Test rod 3.2 mm thick: X-ray detectable with a dose of 0.1 rad
The transparency of each of these moulded items was more than 85%.

These moulded items can therefore be detected in human bodies, even in the shadow of bones, using traditional medical X-ray equipment.

The addition of 4,4'-diiodobiphenyl caused softening of the material. This can be recognised in the reduced glass transition temperature and the lower solution viscosity. Furthermore, it was investigated whether decomposition products of 4,4'-diiodobiphenyl were produced at a processing temperature of 300° C. However, no other products could be found when using GC-MS.

Table 2 summarises trials with other low molecular weight iodine compounds in oligocarbonate melts (molecular weight Mn=1500) at 280° C.:

TABLE 2

Trials with low molecular weight iodine compounds

| Iodine compound | Behaviour in oligocarbonate at 280° C. |
| --- | --- |
| 2,3,5-triiodobenzoic acid | no decomposition, slight discoloration |
| 3,5-diiodosalicylic acid | decomposition with the elimination of iodine, red coloration |
| 4-iodobenzoic acid | no decomposition, bubble formation |

When compared with 4,4'-diiodobiphenyl, the iodine compounds mentioned above exhibited poorer thermal stability for the same X-ray contrast ability.

To summarise, it can be stated that polycarbonate with 4,4'-diiodobiphenyl provides a good x-ray contrast with exceptional mechanical and optical properties.

What is claimed is:

1. X-ray contrastable plastic materials comprising 0.1 wt. % to 25 wt. % of 4,4'-diiodobiphenyl.

2. X-ray contrastable plastics materials comprising:
   at least one low molecular weight iodine compound, wherein the iodine compound is present in amounts of 0.1 wt. % to 25 wt. % and is chosen from the classes D-thyroxin, L-thyroxin, metrizamide, N,N'-bis-(2,3-dihydroxypropyl)-5-[N-(2,3-dihydroxypropyl)-acetamido]-3,4,6-triiodoisophthalamide, α-(2,4,6-triiodophenoxy)-butyric acid, beta-bromo-2,4,6-triiodophenetols, ethylene glycol-4-(iodophenyl)-methylether-methylether and aromatic compounds in accordance with the following general formulae (I), (II), (III)

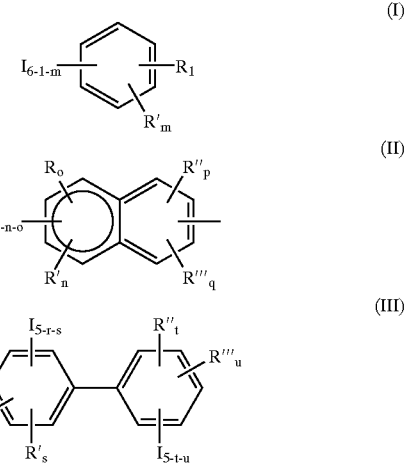

wherein R, R', R'', R''', independently, represent COOH, OH, NHCOR'''', CONHR'''', OR'''', Cl, Br, F, R'''',
where R'''' may be H or a linear or branched alkyl group with 1–18 carbon atoms
and l=0 to 5, m=0 to 5-l, n=0 to 3, o=0 to 3-n, p=0 to 4, q=0 to 4-p, r=0 to 4, s=0 to 4-r, t=0 to 5, u=0 to 5-t, and a group of transparent thermoplastic materials selected from the group consisting of polycarbonates and copolycarbonates based on diphenols, polyacrylates or copolyacrylates based on diphenols, polyacrylates, copolyacrylates and polymethacrylates, transparent polystyrene/acrylonitrile (SAN), transparent cycloolefins, polycondensates or copolycondensates of terephthalic acid.

* * * * *